United States Patent [19]

Regimand

[11] Patent Number: 4,701,868
[45] Date of Patent: Oct. 20, 1987

[54] APPARATUS AND METHOD FOR ACCURATELY MEASURING THE DENSITY OF MATERIALS WITH ROUGH SURFACES BY RADIATION BACKSCATTER

[75] Inventor: Ali Regimand, Raleigh, N.C.

[73] Assignee: Troxler Electronic Laboratories, Inc., Research Triangle Park, N.C.

[21] Appl. No.: 681,303

[22] Filed: Dec. 13, 1984

[51] Int. Cl.$^4$ .......... G06F 15/52; G01V 5/00
[52] U.S. Cl. .................. 364/558; 364/571; 378/89; 250/252.1
[58] Field of Search .......... 364/558, 414, 571; 250/252.1, 256, 266, 308, 358.1, 390 D, 390 E; 378/89, 207

[56] References Cited

U.S. PATENT DOCUMENTS

| 3,539,808 | 11/1970 | Hahn | 378/89 |
| 3,840,746 | 10/1974 | Kehler | 378/89 |
| 3,846,631 | 11/1974 | Kehler | 378/89 |
| 3,900,733 | 8/1975 | Seeman | 250/252.1 |
| 4,587,623 | 5/1986 | Regimand et al. | 250/252.1 |

FOREIGN PATENT DOCUMENTS 0032480 12/1969 Japan .................. 378/89

Primary Examiner—Parshotam S. Lall
Attorney, Agent, or Firm—Bell, Seltzer, Park & Gibson

[57] ABSTRACT

The present invention provides a nuclear radiation backscatter gauge and method by which an accurate determination of the density of a test material can be made, even though the test material may have surface irregularities or voids which would otherwise contribute significant error to the density measurement. The invention is based upon the use of a nuclear density gauge which is specially designed for measuring thin layers, and which is characterized by having a source and at least two separate detector systems mounted in geometrically differing relationships with respect to the source. Through the use of this type of gauge, in combination with a pad or block of known thickness and density, a measurement is made of the density of a top zone of a predetermined thickness which is greater than the thickness of the block and which thus encompasses not only the block but also an upper portion of the underlying material where the surface voids and irregularities exists. A density measurement is also made of the composite material, i.e. the block and the underlying material. The density of the composite material and the density of the top zone are then used to accurately determine the density of the material as it exists below the level of surface irregularities and voids.

9 Claims, 3 Drawing Figures

4,701,868

APPARATUS AND METHOD FOR ACCURATELY MEASURING THE DENSITY OF MATERIALS WITH ROUGH SURFACES BY RADIATION BACKSCATTER

FIELD AND BACKGROUND OF THE INVENTION

The present invention relates to apparatus and methods for determining the density of materials by radiation backscatter, and in particular relates to an improved apparatus and method by which an accurate determination of density can be obtained even though the test material may have a rough or irregular surface.

Nuclear radiation gauges have been widely used for measuring the density of soil and asphaltic materials. Such gauges typically include a source of gamma radiation which is located adjacent the surface of the test material and which directs gamma radiation into the test material, and a radiation detector also located adjacent the surface of the test material for detecting radiation which is reflected or scattered back to the surface. From this detector reading a determination of the density of the material can be made. Such gauges are commonly referred to as "backscatter" gauges.

The gauges commonly in use for measuring the density of soil, asphalt and other materials are most effective at measuring densities of materials over depths of approximately four to six inches. However, with the increasing cost of paving materials, the practice in maintaining and resurfacing paved roadbeds has become one of applying relatively thin layers or overlays one to two inches thick. With layers of such a thickness range, prior density gauges are ineffective for measuring the density of the overlay applied since the density reading which is obtained from such gauges reflects not only the density of the thin layer but also the density of the underlying base material.

Accordingly, efforts have been made to devise a method and device which is capable of accurately determining the density of relatively thin layers of material applied to an underlying base material.

One method which has been developed for measuring the density of thin layers involves the use of a nomograph. By this technique the density of the composite, the density of the underlying base and the thickness of the overlay are separately measured, and the density of the thin overlay is determined by reference to the nomograph. A similar approach, but employing an equation rather than a nomograph, is described in U.S. Pat. No. 4,389,126. These techniques have several shortcomings, most significantly including the necessity of obtaining a density measurement of the base material before application of the thin overlay.

In commonly-owned U.S. patent application Ser. No. 477,820 filed Mar. 22, 1983 entitled "Radiation Scatter Apparatus and Method," U.S. Pat. No. 4,525,854 and in commonly-owned U.S. patent application Ser. No. 681,302, U.S. Pat. No. 4,641,030 filed concurrently herewith and entitled "Apparatus and Method for Directly Measuring the Density of a Thin Layer," there are disclosed apparatus and methods which are capable of directly measuring the density of a thin layer of material without the necessity of making multiple separate density measurements. The apparatus and methods described in the aforementioned commonly-owned copending applications rely upon the use of multiple detector systems for collecting independent sets of data from which the density of the thin top layer can be directly determined.

It has been previously recognized that when making density measurements by the radiation backscatter method, the accuracy is greatest when the surface of the test material is relatively smooth. Rough surfaces tend to produce a low density reading, due to the presence of surface voids or irregularities. This problem becomes particularly troublesome with density measurements of thin layers. Since a density determination of a thin top layer represents a relatively small sample of the material close to the surface, it follows that surface voids and irregularities have a greater influence on the density reading. Consequently, the need exists for a reliable technique to eliminate or correct for inaccuracy due to the presence of surface voids and irregularities when making density measurements of materials which have an irregular or rough surface, especially density measurements of thin layers.

In a study conducted by the California Department of Transportation (CALTRANS) reported in Alexander, M. L. et al "California Study of Asphalt Concrete Density Measurement-Nuclear Versus Core Density," *Placement and Compaction of Asphalt Mixtures*, ASTM STP 829, F. T. Wagner, Ed., American Society for Testing and Materials, 1984, pp. 80–92; the problem of accurately measuring the density of thin surface layers was addressed, and several possible measurement techniques were considered.

One specific approach which was described in this publication was to insert a rubber pad of known density and thickness between a conventional nuclear density gauge and the pavement. The density of the top portion of the pavement could then be determined by measuring the composite density of the pavement and pad and then adjusting for the influence of the pad. The study concluded, however, that the use of a pad of known density and thickness as an interlayer between the gauge and the surface provided no apparent advantage when determining the density of thin layers, and this technique was, therefore, not recommended.

SUMMARY OF THE INVENTION

In accordance with the present invention, a method and apparatus has been developed by which a pad or block of known density and thickness is used for accurately determining the density of a material, including density measurements of thin layers of materials, even though the material may have surface irregularities or voids which would otherwise contribute significant error to the density measurement.

The present invention is based upon the use of a nuclear density gauge which is specially designed for measuring thin layers, and which is characterized by having a source and at least two separate detector systems mounted in geometrically differing relationships with respect to the source. Through the use of this type of gauge, in combination with a pad or block of known thickness and density, whose thickness is less than the effective depth of penetration of the radiation, a measurement is made of the density of a top zone of a predetermined thickness which is greater than the thickness of the block and which thus encompasses not only the block but also an upper portion of the underlying material where the surface voids and irregularities exist. A density measurement is also made by the gauge of the composite material, i.e. the block and the underlying material. The density of the composite material and the density of the top zone are then used to accurately determine the density of the material as it exists below the level of surface irregularities and voids.

BRIEF DESCRIPTION OF THE DRAWINGS

The invention will be more fully understood from the detailed description which follows, when taken in connection with the accompanying drawings, in which—

DESCRIPTION OF THE ILLUSTRATED EMBODIMENT

While the present invention will be described hereinafter with particular reference to the accompanying drawings, it is to be understood at the outset that it is contemplated that the present invention may be varied in specific detail from that illustrated and described herein while still achieving the desirable characteristics and features of the present invention. Accordingly, the description which follows is intended to be understood as a broad enabling disclosure directed to persons skilled in the applicable arts, and is not to be understood as restrictive.

Figure 1:
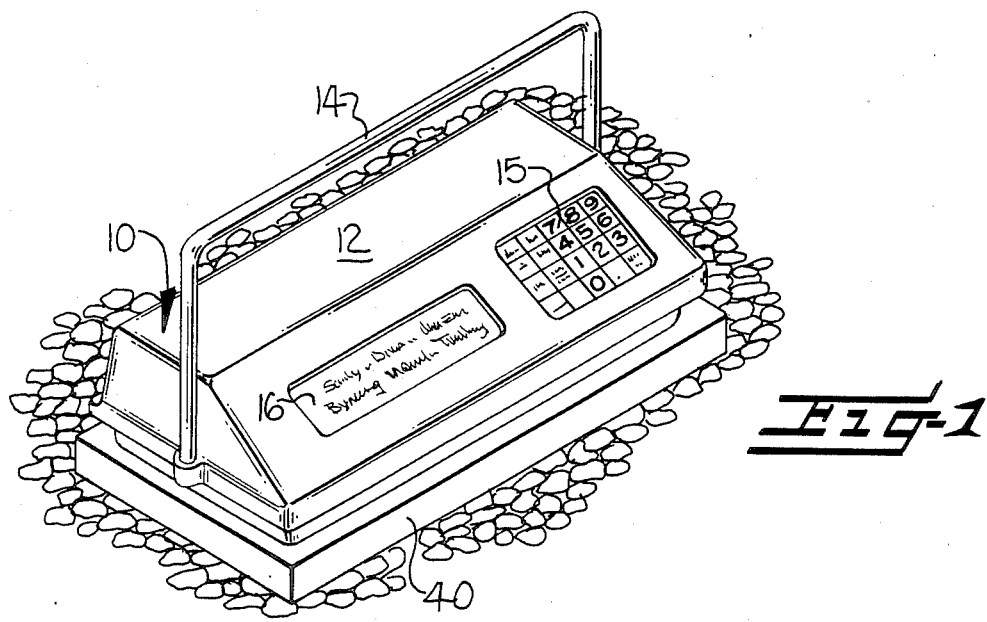
FIG. 1 is a perspective view of a thin layer radiation gauge being used in accordance with the present invention for measuring the density of a material having a rough surface.

Referring now more particularly to the drawings, there is shown in FIG. 1 a radiation gauge 10 constructed in accordance with the invention. The gauge 10 includes a housing, indicated at 12, a handle 14, a keyboard 15, and a display 16. The housing 12 encloses a suitable radiation source 20 (shown in FIG. 2) and two longitudinally spaced apart detector means 22 and 24. The radiation source may be a CS-137 source of gamma radiation and the detector means may take the form of Geiger-Mueller tubes sensitive to photons. As illustrated, the source 20 is located adjacent one end of the base 28 of the housing, and the detector means 22 and 24 are mounted to the base 28 at different longitudinal distances from the source so as to form two geometrically different source to detector relationships. A shielding 30 is provided around the source 20 and around the detectors 22 and 24, as is conventional, to prevent radiation from reaching the detectors in a direct path from the source. Additionally, means (not shown) is provided for completely shielding the radiation source when the gauge is not being used for measurement.

As illustrated, the gauge 10 is positioned on the upper surface of a block 40. Block 40 may be formed of a suitable solid material, preferably a material which has a density less than the density of the test material in order to increase the gauge response. In the illustrated preferred embodiment, the block 40 comprises a solid slab of magnesium one inch in thickness. The block 40 may be conveniently used as a reference standard for taking a standard radiation count for purposes of calibration of the gauge. Persons familiar with the use of nuclear density gauges are aware that for accurate results, a reference count must be taken frequently, typically every day, due to the continuing decay of the nuclear radiation source and to determine that the gauge is operational.

In accordance with the present invention, however, the block 40 also serves another very important function in enabling the gauge 10 to compensate or correct for density error introduced by surface voids or irregularities in the surface of the test material.

Figure 2:
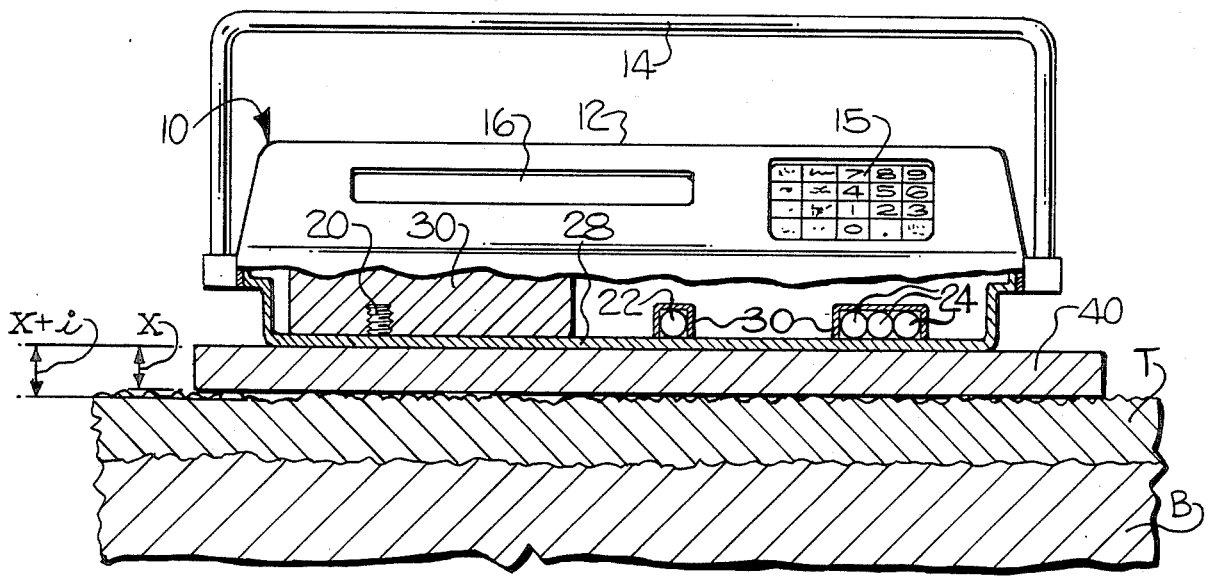
FIG. 2 is a cross sectional view through the lower portion of the gauge, with the gauge resting upon a block, which in turn rests upon a composite test material including a thin top layer applied over an underlying base material.

In the illustrated embodiment, the test material is an asphalt paving material having a relatively rough surface, and the block 40 is positioned on the rough surface of the paving material. As best seen in FIG. 2, the paving material comprises a relatively thin top layer T approximately one to two inches in thickness applied as an overlay on a base material B. The rough upper surface of the top layer T presents numerous voids and irregularities at the interface between the top layer T and the lower surface of block 40.

The nuclear density gauge 10 is specifically designed for directly measuring the density of relatively thin layers. Commonly-owned copending application Ser. No. 681,302, U.S. Pat. No. 4,641,030 filed concurrently herewith and entitled "Apparatus and Method for Directly Measuring the Density of a Thin Layer" describes how the gauge 10 can be used for directly measuring the density of a thin layer of material, and the method and technique described therein is especially useful where the surface of the thin layer is relatively smooth. However, the presence of voids or surface irregularities affects the accuracy of the density reading, especially where the reading is of a relatively thin upper layer.

In the copending application, the gauge 10 relies upon the use of two independent detector systems, wherein the detector systems have differing geometrical relationships with respect to the radiation source. The difference in the geometrical relationships enables the detectors to make separate and distinct radiation measurements that are independent of each other. These independent radiation measurements reflect physical characteristics of the same material, but are weighted more heavily toward different depth strata within the material. Thus, when measurements are made of the same composite material using two detector systems providing two geometrically differing source-to-detector relationships, the equations for the two detector systems are as follows:

$$DG_1 = (D_B - D_T)k_1 + D_T \tag{1}$$

$$DG_2 = (D_B - D_T)k_2 + D_T \tag{2}$$

where $D_{G1}$ and $D_{G2}$ are the gauge density readings of the composite material as determined by the two detector systems, $D_T$ is the density of the top layer of material, $D_B$ is the density of the underlying base material, and $k_1$ and $k_2$ are instrument constants.

Solving for $D_T$, the equations (1) and (2) above may be expressed as follows:

$$D_T = \frac{k_2 D_{G1} - k_1 D_{G2}}{k_2 - k_1} \tag{3}$$

It will thus be seen that from this equation, it is possible to directly determine the density $D_T$ of the top layer based upon two separate and independent gauge density readings $D_{G1}$ and $D_{G2}$, and instrument constants $k_1$ and $k_2$. The constants $k_1$ and $k_2$ are functions of the top layer thickness, top layer density $D_T$ and base density $D_B$. The aforementioned copending patent application describes in detail the procedures which may be employed for determining values for the constants $k_1$ and $k_2$. In the aforementioned copending application, equation (3) above is used for directly measuring the density of the top layer, by using an approximation of the thickness of the top layer, from which the appropriate constants $k_1$ and $k_2$ can be determined.

In accordance with the present invention, the two detector systems of the gauge 10 are employed to measure the error contributed by the surface roughness of the test material. Specifically, by interposing a block 40 of known density and thickness between the test material and the gauge, either of the equations (1) or (2) above can be used in a somewhat different form to determine the density of the base material. By defining a predetermined top zone thickness which is somewhat greater than the known thickness of the block, the density measurement $D_T$ which is obtained through the equation (3) will represent not only the known density of the block, but also the density of a superficial portion of the underlying test material. Thus, as seen in FIG. 2, an increment i is added to the known thickness X of the block 40, such that the top zone thickness (X+i) includes a portion of the top layer T where the roughness and irregularities exist.

For example, where the block 40 has a thickness of one inch, a thickness of, one and one fourth inches may be used as the thickness in equation (3) so that the air gaps, voids and irregularities present in the top one-fourth inch of the top layer will be considered with the magnesium block.

In our example, let us assume that when a density measurement is made utilizing the above equation (3), the density DT of the top zone layer is found to be 107 pounds per cubic foot. The known density of the magnesium block is 110 pounds per cubic foot. The difference between these two values is the error contributed by the voids and irregularities present at the surface of the top layer. Subtracting these two values provides a three pound per cubic foot correction factor.

Now, taking either of the equations (1) or (2) above and solving for $D_B$, the density of the layer underlying the top layer, the following relationship is obtained:

$$D_B = \frac{D_j - D_{TB}(1 - k_j)}{k_j} \tag{4}$$

where j is 1 or 2 and $D_{TB}$ is the known density of the top block.

The thickness X of the block is known, and hence an accurate value for k can be obtained. Similarly, the density $D_{TB}$ for the top layer (the block) is known. $D_j$ is a corrected composite density value which takes into account the error introduced by the top layer, and is obtained from $D_{G1}$ or $D_{G2}$. This is done by adding the three pound per cubic foot correction factor to the gauge density reading. Thus, if $D_{G1}$ read 120, a corrected value of 123 would be used in equation (4) for $D_j$ (where j=1). The resulting value $D_B$ represents the density of the base material as it exists below the surface voids and irregularities.

In practicing the method of the present invention, the block 40 is initially positioned on the surface of the test material, and the gauge 10 is then positioned on the smooth upper surface of the block, as shown in FIGS. 1 and 2. The operator then activates the gauge in the surface roughness measurement mode and selects a suitable time interval over which the radiation count is to be taken. This is conveniently accomplished by pressing appropriate keys on the keyboard 15. In the surface roughness mode of operation, a predetermined value of k+j is automatically used, corresponding to the thickness of the block supplied with the instrument.

The gauge is now ready to determine the density of the test material. Pressing an appropriate key on the keyboard 15 (e.g. "START"), will initiate the reading procedure. At the end of the selected time interval, the total radiation counts detected by each of the two detector systems is obtained, and these values are used to calculate the density of the test material.

The calculations necessary for obtaining the density readings may be carried out by a suitably programmed analog or digital computation device. Preferably, these calculations are carried out by a stored set of instructions in a microprocessor.

Figure 3:
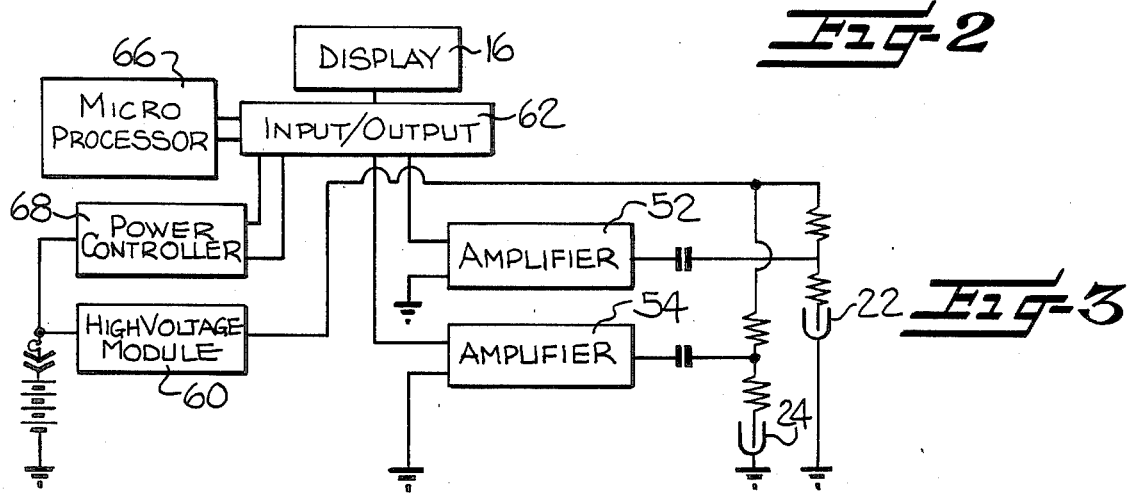
FIG. 3 is a schematic diagram of certain circuit components of the gauge.

Referring to FIG. 3, each of the detectors 22 and 24 is electrically connected with a corresponding amplifier 52, 54. Additionally, as is required, the detectors are connected with a source 60 of high voltage. Outputs from the amplifiers 52 and 54 are directed to an input/output circuit generally indicated at 62 and are available through such circuitry to an electronic computing device shown in the form of a microprocessor 66 and to display 16. Power to the entire device is supplied by a power controller 68.

The microprocessor 66 performs a number of functions including governing the time intervals for gauging in both "Standard" and "Measure" modes. The microprocessor also serves the function of a recorder operatively associated with the detectors for separately recording the measured radiation information from each detector system. In this regard, the radiation information preferably takes the form of a total radiation count for each Geiger-Mueller detector per time interval. In other embodiments the radiation information may take other forms, such as radiation count rates.

The microprocessor also serves to store, in appropriate form, the instructions needed for converting the amplified radiation counts from detector means 22, 24 into values for $D_{G1}$ and $D_{G2}$. Having determined values for $D_{G1}$ and $D_{G2}$, the microprocessor will then calculate the observed density $D_T$ of the predetermined top zone, using the relationship set forth in equation 3, together with appropriate constants $k_1$ and $k_2$ calculated for the top zone thickness (X+i). The microprocessor then compares this resulting value to the known density of the block to determine a correction factor which is added to the previously obtained gauge density readings ($D_{G1}$ or $D_{G2}$). Next, the density $D_B$ of the base material is calculated by the microprocessor using the following relationship:

$$D_B = \frac{D_j - D_{TB}(1 - k_j)}{k_j} \tag{4}$$

In this instance, the value used for the density of the top layer is the known density of the block $D_{TB}$. This value for $D_B$ is displayed to the operator of the machine by the display 16.

It will thus be seen that the present invention provides a novel and advantageous method and apparatus for accurately determining the density of a material having a rough upper surface by means of radiation backscatter and that this accurate determination of density can be made quickly and in a convenient manner in a single operation without the necessity of destructive testing of the test material or of taking multiple readings at different times.

That which is claimed is:

1. A method of measuring the density of a material having a rough upper surface by means of radiation backscatter, said method comprising positioning on the rough upper surface of the material a block of known density and thickness, directing gamma radiation from a source into the block and into the underlying material, obtaining from at least two geometrically differing source-to-detector relationships separate and distinct measurements of radiation scattered from the block and from the underlying material, calculating from said separate and distinct radiation measurements the density of an upper zone of predetermined thickness greater than the thickness of the block and which includes the thickness of the block as well as that portion of the underlying material which forms said rough upper surface, also calculating from at least one of said radiation measurements the composite density of the block and the underlying material, and calculating from said composite density and from said upper zone density the density of the material as it exists below said rough upper surface thereof whereby the density value which is obtained is unaffected by the roughness of the surface of the material.

2. A method of measuring the density of a material having a rough upper surface by means of radiation backscatter, said method comprising positioning on the rough upper surface of the material a block of known density and thickness, directing gamma radiation from a source into the block and into the underlying base material, detecting at two detector locations that are in predetermined geometrical relationship with respect to the source two separate and distinct readings of radiation scattered from the block and from the underlying material and obtaining therefrom respective composite density measurements $D_{G1}$ and $D_{G2}$ of the block and the underlying material, calculating from said composite density measurements $D_{G1}$ and $D_{G2}$ the density $D_T$ of an upper zone of predetermined thickness greater than the thickness of the block and which includes the thickness of the block as well as that portion of the underlying material which forms said rough upper surface, calculating the difference between the measured density $D_T$ of said upper zone of predetermined thickness and the known density of the top block $D_{TB}$ to obtain a correction factor which represents the influence of the surface voids and irregularities present at the upper surface of the base material, correcting at least one of the composite density measurements $D_{G1}$ or $D_{G2}$ by adding said correction factor to obtain a corrected gauge density $D_1$ or $D_2$, and calculating from said corrected composite density $D_j$, where j is 1 or 2, and said known density of the top block $D_{TB}$ the density $D_B$ of the base material as it exists below said rough upper surface thereof whereby the density value which is obtained is unaffected by the roughness of the surface of the material.

3. A method according to claim 2 wherein said step of calculating the density of an upper zone of predetermined thickness comprises calculating the density of the upper zone from the relationship $$D_T = \frac{k_2 D_{G1} - k_1 D_{G2}}{k_2 - k_1}$$

where $D_{G1}$ and $D_{G2}$ are the gauge density readings obtained by said two detector locations and $k_1$ and $k_2$ are instrument constants.

4. A method according to claim 2 wherein said step of calculating the density $D_B$ of the base material comprises calculating the density from the relationship $$D_B = \frac{D_j - D_{TB}(1 - k_j)}{k_j}$$

where j = 1 or 2.

5. An apparatus for measuring the density of a material having a rough upper surface by means of radiation backscatter, said apparatus comprising a block of material of known density and thickness adapted to be positioned on the rough surface of the test material, means for emitting nuclear radiation from a source into said block and into the underlying test material and for detecting radiation which is scattered therefrom at two geometrically differing source-to-detector relationships, first calculating means for responding to the detected radiation at said two source-to-detector relationships and for obtaining therefrom respective composite density measurements of the block and the underlying materials, second calculating means for calculating from said respective composite density measurements the density of an upper zone of predetermined thickness greater than the thickness of said block and which includes the thickness of the block as well as that portion of the underlying material which forms said rough upper surface, and third calculating means for calculating from said composite density and said upper zone density the density of the material as it exists below said rough upper surface thereof whereby the density value which is obtained is unaffected by the roughness of the surface of the material.

6. An apparatus for measuring the density of a material having a rough upper surface by means of radiation backscatter, said apparatus comprising a block of material of known density and thickness adapted to be positioned on the rough surface of the test material, source means for emitting gamma radiation into said block and into the underlying test material, detector means including at least two radiation detectors located in predetermined spaced relation to said source for obtaining respective radiation measurements which are distinctive from the radiation measured by any other detector, first calculating means operatively associated with said detector means for obtaining respective composite density measurements of the block and the underlying materials, second calculating means for calculating from said respective composite density measurements the density of an upper zone of predetermined thickness greater than the thickness of said block and which includes the thickness of the block as well as that portion of the underlying material which forms said rough upper surface, and third calculating means for calculating from said composite density and said upper zone density the density of the material as it exists below said rough upper surface thereof whereby the density value which is obtained is unaffected by the roughness of the surface of the material.

7. Apparatus according to claim 6 wherein said block comprises a substantially flat block of metal.

8. Apparatus according to claim 7 wherein the metal is magnesium.

9. Apparatus according to claim 6 wherein said first, second and third calculating means comprise respective sets of instructions embodied in a microprocessor.

* * * * *